US008582089B2

(12) United States Patent
Nelson et al.

(10) Patent No.: US 8,582,089 B2
(45) Date of Patent: Nov. 12, 2013

(54) SYSTEM AND METHOD FOR COMBINED RAMAN, SWIR AND LIBS DETECTION

(75) Inventors: Matthew Nelson, Harrison City, PA (US); Patrick Treado, Pittsburgh, PA (US); Charles W Gardner, Jr., Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 378 days.

(21) Appl. No.: 12/899,119

(22) Filed: Oct. 6, 2010

(65) Prior Publication Data

US 2011/0080577 A1 Apr. 7, 2011

Related U.S. Application Data

(63) Continuation-in-part of application No. 12/199,145, filed on Aug. 27, 2008, now Pat. No. 8,054,454, which is a continuation of application No. 11/450,149, filed on Jun. 9, 2006, now Pat. No. 7,692,775.

(51) Int. Cl.
*G01N 21/00* (2006.01)

(52) U.S. Cl.
USPC .......................................................... 356/73

(58) Field of Classification Search
USPC .................. 356/72–73, 301, 318; 250/339.11
See application file for complete search history.

(56) References Cited

U.S. PATENT DOCUMENTS

| 4,880,052 A | 11/1989 | Meyer |
| 5,194,912 A | 3/1993 | Batchelder |
| 5,377,004 A | 12/1994 | Owen |
| 5,442,438 A | 8/1995 | Batchelder |
| 5,528,368 A | 6/1996 | Lewis |
| 5,528,393 A | 6/1996 | Sharp |
| 5,539,517 A | 7/1996 | Cabib |
| 5,606,164 A | 2/1997 | Price |
| 5,623,342 A | 4/1997 | Baldwin et al. |
| 5,689,333 A | 11/1997 | Batchelder |
| 5,710,626 A | 1/1998 | O'Rourke |
| 5,862,273 A | 1/1999 | Pelletier |
| 5,866,430 A | 2/1999 | Grow |

(Continued)

FOREIGN PATENT DOCUMENTS

| EP | 2083259 | 7/2009 |
| JP | 9121889 | 5/1997 |

(Continued)

OTHER PUBLICATIONS

Wiens et al., "Joint Analysis by Laser-Induced Breakdown Spectroscopy (LIBS) and Raman Spectroscopy at Standoff Systems", 2005, Spectrochemica Acta Part A, 61, pp. 2324-2334.*

(Continued)

*Primary Examiner* — Kara E Geisel

(57) ABSTRACT

A system and method for the detection and identification of explosives and explosive residues using a combination of SWIR, Raman, and LIBS spectroscopy techniques, including imaging. A region of interest may be surveyed to identify a target area, wherein the target area comprises at least one unknown material. This surveying may be accomplished using visible imagery or SWIR imagery. The target area may be interrogated using Raman spectroscopy and LIBS spectroscopy to identify the unknown material. SWIR techniques may also be used to interrogate the target area. Fusion algorithms may also be applied to visible images, SWIR data sets, Raman data sets, and/or LIBS data sets.

26 Claims, 3 Drawing Sheets

(56) References Cited

U.S. PATENT DOCUMENTS

| | | | |
|---|---|---|---|
| 5,901,261 A | 5/1999 | Wach | |
| 5,911,017 A | 6/1999 | Wach | |
| 6,002,476 A | 12/1999 | Treado | |
| 6,008,492 A | 12/1999 | Slater | |
| RE36,529 E | 1/2000 | Lewis | |
| 6,075,891 A | 6/2000 | Burman | |
| 6,208,749 B1 | 3/2001 | Gutkowicz-Krusin | |
| 6,421,553 B1 | 7/2002 | Costa et al. | |
| 6,717,668 B2 | 4/2004 | Treado et al. | |
| 6,954,667 B2 | 10/2005 | Treado | |
| 6,965,793 B2 | 11/2005 | Treado | |
| 6,967,612 B1 | 11/2005 | Gorman | |
| 6,985,216 B2 | 1/2006 | Treado | |
| 6,992,809 B1 | 1/2006 | Wang | |
| 7,012,695 B2 | 3/2006 | Maier | |
| 7,019,296 B2 | 3/2006 | Treado | |
| 7,061,606 B2 | 6/2006 | Treado | |
| 7,068,357 B2 | 6/2006 | Treado | |
| 7,072,770 B1 | 7/2006 | Schweitzer | |
| 7,088,435 B2 | 8/2006 | Brestel | |
| 7,123,360 B2 | 10/2006 | Treado | |
| 7,161,672 B2 | 1/2007 | Gornuskin | |
| 7,268,861 B2 | 9/2007 | Treado | |
| 7,268,862 B2 | 9/2007 | Treado | |
| 7,277,178 B2 | 10/2007 | Shpantzer et al. | |
| 7,295,308 B1 | 11/2007 | Samuels | |
| RE39,977 E | 1/2008 | Treado | |
| 7,317,516 B2 | 1/2008 | Treado | |
| 7,322,267 B1 | 1/2008 | Munson | |
| 7,362,489 B2 | 4/2008 | Wang | |
| 7,362,839 B2 | 4/2008 | Goth | |
| 7,409,299 B2 | 8/2008 | Schweitzer | |
| 7,417,727 B2 | 8/2008 | Polonskiy | |
| 7,417,796 B2 | 8/2008 | Wang | |
| 7,420,664 B2 | 9/2008 | Treado et al. | |
| 7,436,500 B2 | 10/2008 | Treado | |
| 7,474,685 B2 | 1/2009 | Kalayeh | |
| 7,479,966 B2 | 1/2009 | Maier | |
| 7,502,188 B2 | 3/2009 | Inomata | |
| 7,511,624 B2 | 3/2009 | Shaw | |
| 7,525,102 B1 | 4/2009 | Henshaw | |
| 7,542,138 B2 | 6/2009 | Gardner | |
| 7,551,715 B2 | 6/2009 | Rothschild | |
| 7,679,740 B2 | 3/2010 | Neiss | |
| 7,692,775 B2 | 4/2010 | Treado | |
| 7,705,981 B2 | 4/2010 | Maier | |
| 2001/0052979 A1 | 12/2001 | Treado | |
| 2003/0085348 A1 | 5/2003 | Megerle | |
| 2003/0123056 A1 | 7/2003 | Barnes | |
| 2004/0051867 A1 | 3/2004 | Brestel | |
| 2005/0105099 A1 | 5/2005 | Shpantzer | |
| 2005/0264813 A1 | 12/2005 | Giakos | |
| 2006/0077377 A1 | 4/2006 | Brestel | |
| 2006/0100524 A1 | 5/2006 | Lucassen | |
| 2006/0170922 A1 | 8/2006 | Wang | |
| 2006/0203238 A1 | 9/2006 | Gardner | |
| 2006/0219937 A1 | 10/2006 | Henry | |
| 2006/0254522 A1 | 11/2006 | Shaw | |
| 2006/0256330 A1 | 11/2006 | Leipertz | |
| 2006/0262304 A1 | 11/2006 | Carron | |
| 2007/0007384 A1 | 1/2007 | Sliwa | |
| 2007/0098142 A1 | 5/2007 | Rothschild | |
| 2007/0125951 A1 | 6/2007 | Snider | |
| 2007/0127030 A1 | 6/2007 | Shpantzer | |
| 2007/0139772 A1 | 6/2007 | Wang | |
| 2007/0153268 A1 | 7/2007 | Panza | |
| 2007/0166045 A1 | 7/2007 | Wang | |
| 2007/0192035 A1 | 8/2007 | Schweitzer | |
| 2007/0268485 A1 | 11/2007 | Polonskiy et al. | |
| 2008/0036593 A1 | 2/2008 | Rose-Pehrsson | |
| 2008/0062353 A1 | 3/2008 | Wang | |
| 2008/0084553 A1 | 4/2008 | Neiss | |
| 2008/0088837 A1 | 4/2008 | Gardner | |
| 2008/0129581 A1 | 6/2008 | Douglas | |
| 2008/0144885 A1 | 6/2008 | Zucherman | |
| 2008/0165344 A1 | 7/2008 | Treado | |
| 2008/0191137 A1 | 8/2008 | Poteet | |
| 2008/0192246 A1 | 8/2008 | Neiss | |
| 2008/0198365 A1 | 8/2008 | Treado | |
| 2008/0204757 A1 | 8/2008 | Manning | |
| 2008/0258071 A1 | 10/2008 | Arnold | |
| 2008/0268548 A1 | 10/2008 | Zuckerman | |
| 2008/0295783 A1 | 12/2008 | Furton | |
| 2008/0300826 A1 | 12/2008 | Schweitzer | |
| 2009/0012723 A1 | 1/2009 | Treado | |
| 2009/0021730 A1 | 1/2009 | Maier | |
| 2009/0043514 A1 | 2/2009 | Schweitzer | |
| 2009/0046393 A1 | 2/2009 | Davey | |
| 2009/0066947 A1 | 3/2009 | Bangalore | |
| 2009/0095885 A1 | 4/2009 | Hager | |
| 2009/0101843 A1 | 4/2009 | Henshaw | |
| 2009/0128802 A1 | 5/2009 | Treado | |
| 2009/0236528 A1 | 9/2009 | Shpantzer | |
| 2009/0252650 A1 | 10/2009 | Lakshmanan | |
| 2009/0257555 A1 | 10/2009 | Chalmers | |
| 2010/0051809 A1 | 3/2010 | Onat | |
| 2012/0147358 A1* | 6/2012 | Gardner et al. | 356/72 |

FOREIGN PATENT DOCUMENTS

| | | |
|---|---|---|
| WO | PCT/US05/25112 | 2/2006 |
| WO | PCT/IB2006/052448 | 1/2007 |
| WO | PCT/US2005/036593 | 1/2007 |
| WO | PCT/US2006/027172 | 3/2007 |
| WO | PCT/US2006/060158 | 3/2007 |
| WO | PCT/US2005/033740 | 4/2007 |
| WO | PCT/US2006/012300 | 4/2007 |
| WO | PCT/US2006/060683 | 5/2007 |
| WO | PCT/US2005/044648 | 7/2007 |
| WO | PCT/US06/22647 | 11/2007 |
| WO | PCT/US2007/015132 | 3/2008 |
| WO | PCT/US2007/018347 | 4/2008 |
| WO | PCT/US2007/081551 | 4/2008 |
| WO | PCT/US2007/016040 | 8/2008 |

OTHER PUBLICATIONS

Sharma, et al., Standoff Raman Spectroscopic Detection of Minerals on Planetary Surfaces, Hawaii Institute of Geophysics and Planetology, pp. 2391-2407, 2003.

Sharma et al., "Remote Pulsed Laser Raman Spectroscop System for Mineral Analysis on Planetary Surfaces to 66 Maters", Applied Spectroscopy, vol. 56, No. 6, 2002, pp. 669-705.

International Search Report, PCT/US06/22647, mailed on Mar. 31, 2008.

Onat, Bora et al, "Solid State Hyperspectral Imager for Real Time Standoff Explosive Detection Using Short Wave Infrared Imaging," Proc. of SPIE vol. 7310, 731004-1 to 731004-11, 2009.

Clegg, S.M et al, LIBS-Raman Spectroscopy of Minerals Using Remote Surface Modification Techniques. Mar. 2006, Lunar Planet Sci. XXXVII.

Thompson, J. et al, Combined Remote LIBS and Raman Spectroscopy Measurements, Lunar Plant Sci, XXXVI.

Weins, R.C., "Development of Prototype Laser-Induced Breakdown Spectroscopy (LIBS) Instrument and Standoff Raman Capabilities as Part of the Mars Instrument Development Program," Lunar Plant Sci. XXXI.

Poster Session: Mars Polar Science. Astrobiology, Future Missions/ Instruments and Other Mars Science, Jul. 2007, Seventh International Conference on Mars. Session 11.

Marguardt, et al, "Novel Probe for Laser-Induced Breakdown Spectroscopy and Raman Measurements Using an Imaging Optical Fiber," Jun. 1998, vol. 52, No. 9.

Nelson et al, "Single-Shot Multiwavelength Imaging of Laser Plumes," Applied Spectroscopy, vol. 52. No. 2, Feb. 1, 1998.

Extended European Search Report, PCT/US2006/022647, Mailed Aug. 10, 2010.

Caetano et al., "Evaluation of the Importance of Non-Linear Spectral Mixing in Coniferous Forests," SPIE vol. 3499, Sep. 1998, pp. 257-269.

(56) References Cited

OTHER PUBLICATIONS

Rasmussen et al, "Library Retrieval of Infrared Spectra Based on Detailed Intensity Information," Applied Spectroscopy, vol. 33, No. 4, Feb. 1979, pp. 371-376.

Guilment et al., "Infrared Chemical Micro-Imaging Assisted by Interactive Self-Modeling Multivariate Analysis," Applied Spectroscopy, vol. 48, No. 3, 1994, pp. 320-326.

Malinowski, :Facor Anayss in Chemistry, 1991, 2nd Edition, Published by John Wiley and Sons, Inc. William H. Press, et al, pp. 208-265.

Marquardt, et al, "Novel Probe for Laser-Induced Breakdown Spectroscopy and Raman Measurements Using an Imaging Optical Filter," Applied Spectroscopy, 1998, p. 1148-1153, vol. 52, No. 9.

Thompson et al, Combined Remote LIBS and Raman Spectroscopy Measurements, Lunar and Planetary Science Conference, XXXVI, #1517, Houston, Texas, Mar. 14-18, 2005, (*available at : http://www.lpi.ursa.edu/meetings/lpsc2005/pdf/1517.pdf), last accessed Sep. 23, 2008.

Hubble et al, A Combined Remote LIBS and Raman Spectroscopy Study of Minerals, Lunar and Planetary Science Conference, XXXIII, #1935, Houston, Texas, Mar. 11-15, 2002, (Available at: http:www.lpi.usra.edu/meetings/lpsc2002/pdf/1935.pdf), last accessed Sep. 23, 2008.

Sharma et al, Portable Standoff Raman and Mie-Rayieigh Lidar for Cloud, Aerosols, and Chemical Monitoring, Proceedings of SPIE vol. 5154 Lidar Remote Sensing for Environmental Monitoring IV, pp. 1-14, 2003.

Sharma, S.K. et al, Combined Remote LIBS and Raman Spectroscopy of Minerals Using a Single Laser Source, Lunar Plant Sci, XXXVII, 2007.

* cited by examiner

SYSTEM AND METHOD FOR COMBINED RAMAN, SWIR AND LIBS DETECTION

RELATED APPLICATION

This Application is a continuation-in-part of pending U.S. patent application Ser. No. 12/199,145, filed on Aug. 27, 2008, entitled "Time and Space Resolved Standoff Hyperspectral IED Explosives LIDAR Detector," which itself claims priority to U.S. Pat. No. 7,692,775, filed on Jun. 9, 2006, also entitled "Time and Space Resolved Standoff Hyperspectral IED Explosives LIDAR Detector." This Application also claims priority to the following U.S. Provisional Patent Application No. 61/335,785, filed on Jan. 12, 2010, entitled "System and Method for SWIR HSI for Daytime and Nighttime Operations," No. 61/278,393, filed on Oct. 6, 2009, entitled "Use of Magnification to Increase SWIR HSI Detection Sensitivity," No. 61/301,814, filed on Feb. 5, 2010, entitled "System and Method for Detecting Hazardous Agents Including Explosives," No. 61/305,667, filed on Feb. 18, 2010, entitled "System and Method for Detecting Explosives on Shoes and Clothing," No. 61/403,141, filed on Sep. 10, 2010, entitled "Systems and Methods for Improving Imaging Technology", No. 61/324,963, filed on Apr. 16, 2010, "Short-Wavelength Infrared (SWIR) Multi-Conjugate Liquid Crystal Tunable Filter." These patent and patent applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopy. When applied to the chemical analysis of materials, spectroscopic imaging is commonly referred to as chemical imaging.

Instruments for performing spectroscopic (i.e. chemical) imaging typically comprise an illumination source, image gathering optics, focal plane array imaging detectors and imaging spectrometers. In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters is actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

There currently exists a need to enable accurate and reliable detection of explosives and other hazardous materials. There also exists a need to configure such detection systems and methodologies to operate in a variety of modalities including, but not limited to: proximal, standoff, stationary, and on-the-move.

SUMMARY OF THE INVENTION

The present disclosure generally relates to systems and methods for the detection of explosives and other hazardous agents using spectroscopic systems and methods. More specifically, the present disclosure relates to the implementation of a combination of Raman, short wave infrared (SWIR), and laser induced breakdown spectroscopy (LIBS) spectroscopic techniques for the detection and identification of explosive materials. Structured illumination may be used or simultaneous or sequential acquisition of multiple data types. Autofocus, auto-calibration, auto-alignment, and auto-targeting functionalities may also be implemented.

The present disclosure also provides for the use of a single laser, multiple excitation design to provide better overall coverage for materials of interest. The present disclosure also provides for multi-aperture Raman sensing for improved ease of interrogation and enhanced sensitivity. The present disclosure also provides for laser interlocking upon the detection of humans in a scene, to improve the overall safety of explosives detection.

DETAILED DESCRIPTION

The accompanying drawings, which are included to provide further understanding of the disclosure and are incorporated in and constitute a part of this specification, illustrate embodiments of the disclosure and, together with the description, serve to explain the principles of the disclosure.

The present disclosure provides for embodiments of a system and method for detecting and identifying explosive materials. In one embodiment, a method of the present disclosure provides for the use of a combination of Raman, SWIR, and LIBS spectroscopic data to facilitate such detection and identification. In one embodiment, Raman interrogation may comprise UV/Raman interrogation. In one embodiment, these techniques may be used in a targeting mode and/or and identification mode. In a targeting mode, a region of interest may be surveyed to thereby identify a target area within the region of interest that comprises an unknown material. This target area may then be subject to further analysis to thereby identify the unknown material. The present disclosure also contemplates that visible imaging may also be used in a targeting mode to survey an area of interest.

Figure 1:
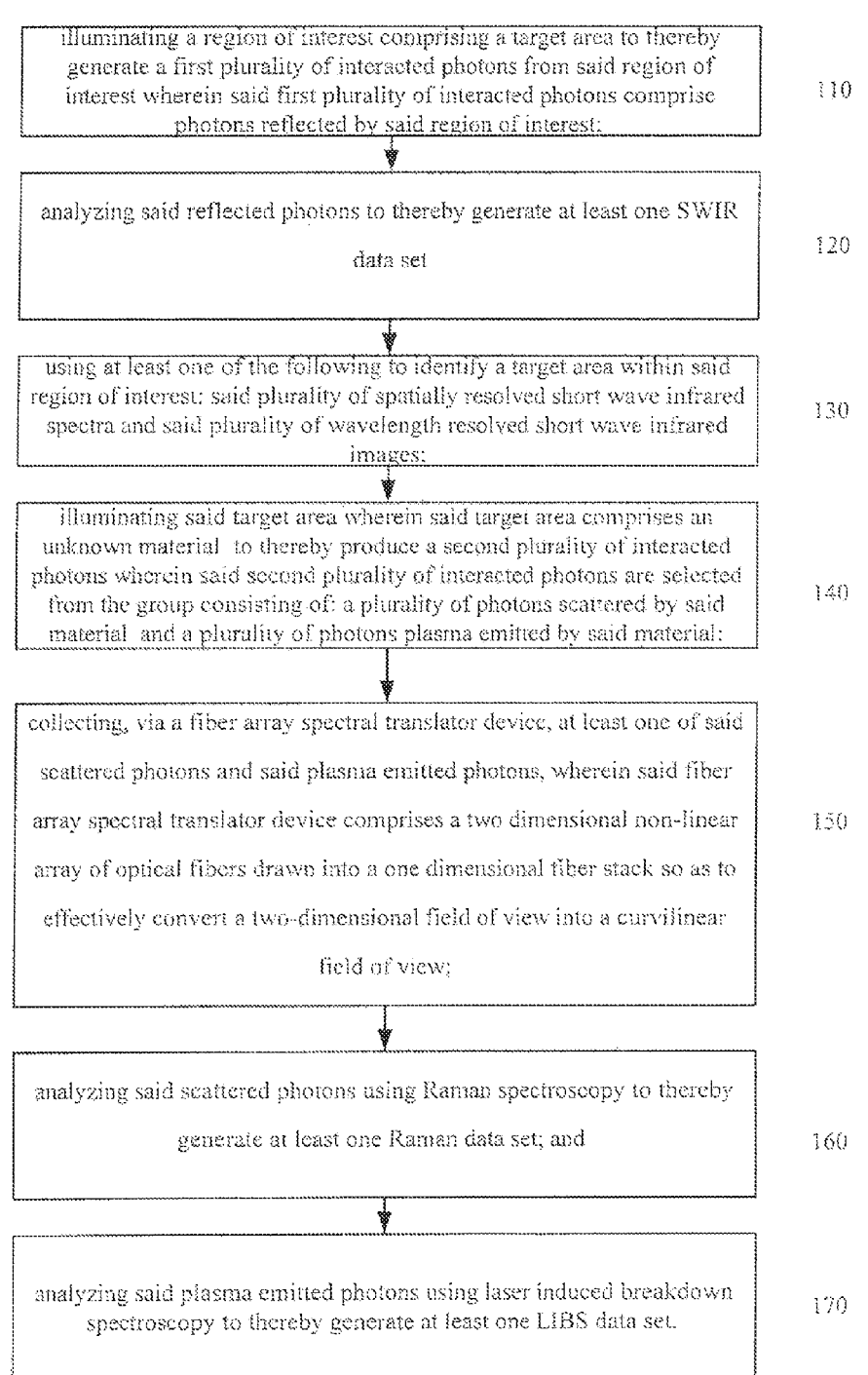
FIG. 1 is representative of a method of the present disclosure.

FIG. 1 is representative of a method of the present disclosure wherein SWIR spectroscopic techniques are used to target and Raman and/or SWIR techniques are used to identify. The method 100 comprises illuminating a region of interest comprising a target area to thereby generate a first plurality of interacted photons from said region of interest in step 110. In one embodiment, illustrated by FIG. 1, the first plurality of interacted photons may comprise photons reflected from said region of interest. In step 120 these reflected photons are analyzed to thereby generate at least one SWIR data set representative of said region of interest. In one embodiment, the SWIR data set may comprise at least one of: a plurality of spatially resolved SWIR spectra and a plurality of spatially resolved SWIR images. In one embodiment, the SWIR data set may comprise a SWIR hyperspectral image. The SWIR hyperspectral image may comprise an image and a fully resolved SWIR spectra for each pixel in the image. In one embodiment, the SWIR data set may comprise a dynamic chemical image, which may comprise a dynamic SWIR hyperspectral image.

In step 130 the SWIR data set may be analyzed to identify a target area within the region of interest. In step 140 the target area is illuminated, wherein the target area comprises an unknown material, to thereby generate a second plurality of interacted photons. In one embodiment, this second plurality of interacted photons may comprise at least one of: photons scattered by said target area, photons plasma emitted by said target area, and combinations thereof. In step 150 at least one of the scattered photons and plasma emitted photons are collected via a fiber array spectral translator device (FAST). In one embodiment, a fiber array spectral translator device may improve targeting abilities and increase image fidelity. In one embodiment, the fiber array spectral translator device may comprise a two-dimensional non-linear array of optical fibers drawn into a one-dimensional fiber stack so as to effectively convert a two-dimensional field of view into a curvilinear field of view. In step 160 the scattered photons are analyzed using Raman spectroscopy to thereby generate a Raman data set representative of said target area. In one embodiment, the Raman data set may comprise a plurality of spatially resolved Raman spectra and a plurality of spatially resolved Raman images. In one embodiment the Raman data set may comprise a Raman hyperspectral image. The Raman hyperspectral image may comprise an image and a fully resolved Raman spectra for each pixel in the image. In one embodiment, the Raman data set may comprise a dynamic chemical image, which may comprise a dynamic Raman hyperspectral image.

In step 170 said plasma emitted photons may be analyzed using LIBS spectroscopy to thereby generate a LIBS data set representative of the target area. In one embodiment, the LIES data set may comprise at least one of a plurality of spatially resolved LIBS spectra and a plurality of spatially resolved LIBS images. In one embodiment, the LIBS data set may comprise a LIBS hyperspectral image. The LIBS hyperspectral image may comprise an image and a fully resolved LIBS spectra for each pixel in the image. In one embodiment, the LIBS data set may comprise a dynamic chemical image, which may comprise a dynamic LIBS hyperspectral image.

The method 100 may further comprise applying a fusion algorithm to at least one of said Raman data set and said LIBS data set. In one embodiment, this fusion may be accomplished using software. In one embodiment, this fusion software may comprise ChemImage's FIST ("Forensic Integrated Search") technology, available from ChemImage Corporation, Pittsburgh, Pa. This technology is more fully described in pending U.S. patent application Ser. Nos. 11/450,138, filed on Jun. 9, 2006, entitled "Forensic Integrated Search Technology"; 12/017,445, filed on Jan. 22, 2008, entitled "Forensic Integrated Search Technology with Instrument Weight Factor Determination"; 12/196,921, filed on Aug. 22, 2008, entitled "Adaptive Method for Outlier Detection and Spectral Library Augmentation"; and 12/339, 805, filed on Dec. 19, 2008, entitled "Detection of Pathogenic Microorganisms Using Fused Sensor Data". Each of these applications are hereby incorporated by reference in their entireties.

In another embodiment, the present disclosure provides for ChemFusion Improvements. Such improvements include the use of grid search methodology to establish improved weighting parameters for individual sensor modality classifiers under JFIST Bayesian architecture. In another embodiment, image weighted Bayesian fusion may be used.

Figure 2:
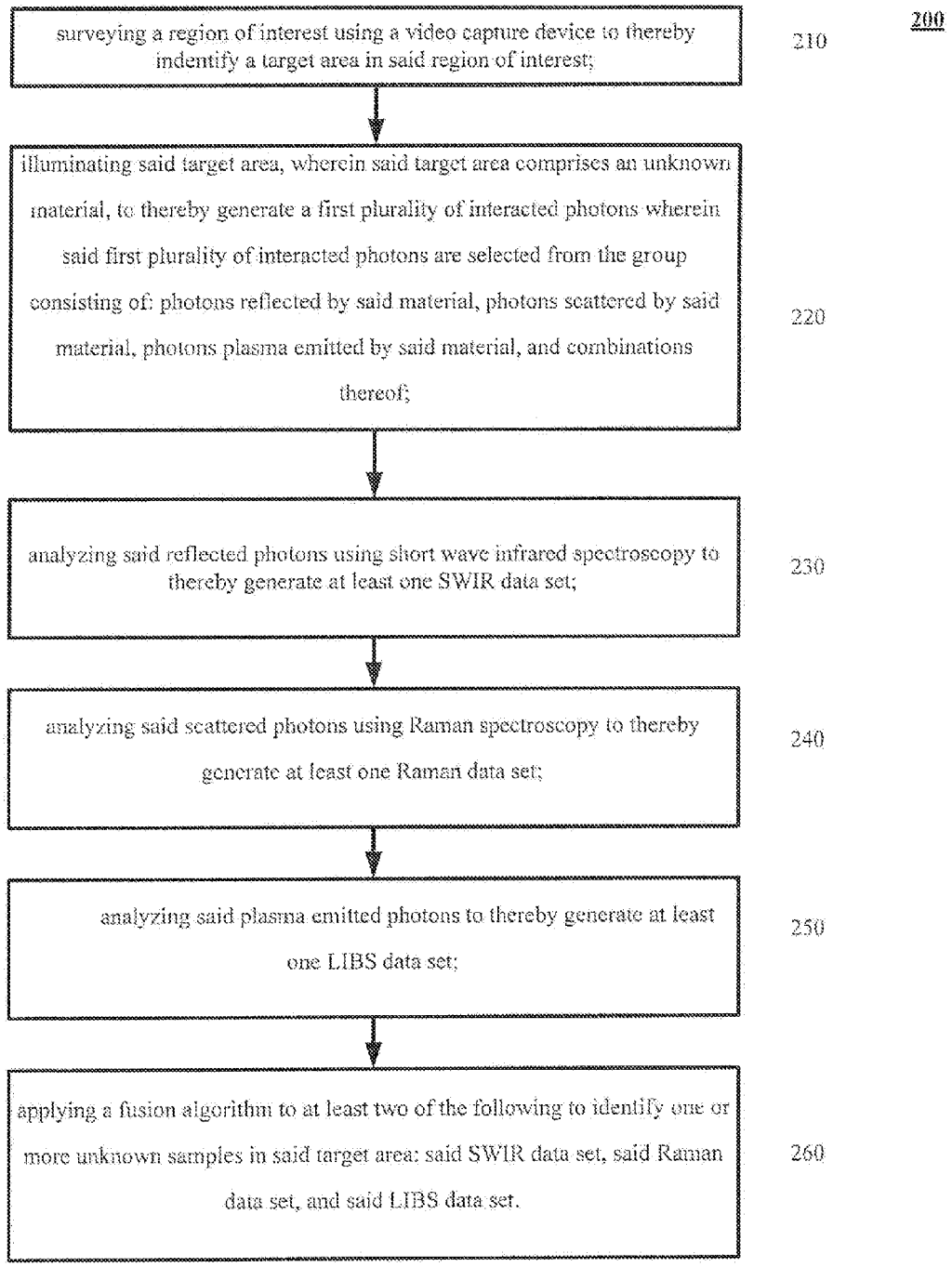
FIG. 2 is representative of a method of the present disclosure.

In another embodiment, the present disclosure provides for a method, illustrated by FIG. 2 wherein visible imaging techniques are used to target and a combination of Raman, SWIR, and/or LBS is used to identify. The method 200 may comprise surveying a region of interest, in step 210, using a video capture device to thereby identify a target area in said region of interest. In step 220 the target area may be illuminated, wherein the target area comprises an unknown material, to thereby generate a first plurality of interacted photons. In one embodiment, this first plurality of interacted photons may comprise photons selected from the group consisting of: photons reflected by said target area, photons scattered by said target area, photons plasma emitted by said target area, and combinations thereof.

In step 230 the reflected photons may be analyzed using SWIR spectroscopy to generate a SWIR data set representative of the target area. In one embodiment, the SWIR data set may comprise at least one of: a plurality of spatially resolved SWIR spectra and a plurality of spatially resolved SWIR images. In one embodiment, the SWIR data set may comprise a SWIR hyperspectral image. The SWIR hyperspectral image may comprise an image and a fully resolved SWIR spectra for each pixel in the image. In one embodiment, the SWIR data set may comprise a dynamic chemical image, which may comprise a dynamic SWIR hyperspectral image.

In step 240 the scattered photons may be analyzed using Raman spectroscopy to thereby generate a Raman data set representative of the target area. In one embodiment, the Raman data set may comprise a plurality of spatially resolved Raman spectra and a plurality of spatially resolved Raman images. In one embodiment the Raman data set may comprise a Raman hyperspectral image. The Raman hyperspectral image may comprise an image and a fully resolved Raman spectra for each pixel in the image. In one embodiment, the Raman data set may comprise a dynamic chemical image, which may comprise a dynamic Raman hyperspectral image.

In step 250 the plasma emitted photons may be analyzed using LIBS spectroscopy to thereby generate a LIBS data set representative of said target area. In one embodiment, the LIBS data set may comprise at least one of a plurality of spatially resolved LIBS spectra and a plurality of spatially resolved LIBS images. In one embodiment, the LIBS data set may comprise a LIBS hyperspectral image. The LIBS hyperspectral image may comprise an image and a fully resolved LIBS spectra for each pixel in the image. In one embodiment, the LIBS data set may comprise a dynamic chemical image, which may comprise a dynamic LIBS hyperspectral image.

In step 260 the method may further comprise applying a fusion algorithm to at least one of: the SWIR data set, the Raman data set, and the LIBS data set to thereby identify one or more unknown materials present in said target area.

The methods of the present disclosure contemplate the detection and identification of unknown materials present in at least one of a region of interest and/or a target area in said region of interest. In one embodiment, this unknown material may comprise an explosive material, a non-explosive material, a explosive residue, a material associated with an explosive material, and combination thereof. Explosive materials that may be detected using the system and method disclosed herein include, but are not limited to: nitrocellulose, Ammonium nitrate ("AN"), nitroglycerin, 1,3,5-trinitroperhydro-1, 3,5-triazine ("RDX"), 1,3,5,7-tetranitroperhydro-2,3,5,7-tetrazocine ("HMX") and 1,3,-Dinitrato-2,2-bis(nitratomethyl) propane ("PETN").

The present disclosure contemplates the surveying of a region of interest to thereby target a target area, wherein the target area comprises at least one unknown material. The present disclosure contemplates a variety of objects, surfaces, and environments may comprise the region of interest, target area, and unknown material. These may include, but are not limited to: sand, cement, disturbed earth, command wires, foam, plastic, elements found in nature, a ground vehicle, an airplane/aircraft, a boat or other water vehicle, a human, a human body part, an article of clothing (including shoes), an identifying document (such as a passport, boarding pass, ticket, driver's license), a piece of luggage, briefcase, purse, wallet, and combinations thereof. Additionally, the present disclosure contemplates that both above ground areas and below ground areas may be interrogated using the system and method disclosed herein.

The embodiments of the methods disclosed herein contemplate the use of visible imaging devices to survey at least one of a region of interest and a target area. This visible imaging device may comprise: a video capture device, a RGB camera, and combinations thereof. This visible imaging device may output a dynamic image of at least one of a region of interest and a target area.

The embodiments of the methods disclosed herein contemplate that illumination of at least one of the region and interest and the target area may be achieved using structured illumination. In one embodiment this structured illumination may comprise illuminating a first region of a region of interest/target area with a first illumination pattern and a second region of a region of interest/target area with a second illumination pattern. In one embodiment, the first region may be illuminated using a first excitation wavelength and the second region may be illuminated using a second excitation wavelength. In another embodiment, the same excitation wavelength may be used to illuminate the first region and the second region.

In one embodiment, the first region and the second region may be illuminated sequentially. In another embodiment, the first region and the second region may be illuminated simultaneously.

Additionally, the present disclosure contemplates that this illumination configuration, inducing the use of structured illumination, can be used to illuminate a number of regions of a region of interest and/or target area and is not limited to the illumination of a first region and a second region. For example, the illumination configuration disclosed herein may be applied to a third region of a region of interest and/or target area.

In one embodiment, the methods of present disclosure provide for the illumination of at least one of the region of interest and the target area with an illumination source selected from the group consisting of: a laser light source, a broadband light source, an ambient light source and combinations thereof. Therefore, the methods disclosed herein may operate in an active illumination mode and a passive illumination mode. The methods may also operate in a hybrid active/passive illumination mode. For example, in such a hybrid mode, an ambient light source, such as the sun, may be used for SWIR data acquisition and an active light source, such as a laser light source, may be used for Raman and/or LIBS data acquisition.

In one embodiment, the method of the present disclosure may illuminate at least one of the region of interest and/or the target area using at least one of: continuous wave laser excitation, pulsed laser excitation, and combinations thereof.

In another embodiment, the method of the present disclosure may provide for the time-gated detection of the photons reflected, scattered, and/or plasma emitted by the sample. In such an embodiment, an illumination source may be operatively coupled to one or more detection devices so as to acquire Raman, SWIR, and/or LIBS data in accordance with Raman, SWIR, and/or LIBS emission times. The use of pulsed laser excitation and time-gated detection is more fully described in U.S. patent application Ser. No. 12/802,994, filed on Jun. 17, 2010, which is hereby incorporated by reference in its entirety.

The methods of the present disclosure may further utilize telescope optics to thereby locate and/or focus on a region of interest and/or target area. The telescope optics may also be utilized to collect at least one of the photons reflected, scattered, and/or plasma emitted by at least one of a region of interest and a target sample.

The methods of the present disclosure may further comprise passing at least one of the photons reflected, scattered, and/or plasma emitted from at least one of the region of interest and/or the target area through a tunable filter, or other spectrographic device. In one embodiment, the tunable filter may be a filter selected from the group consisting of: a SWIR multi-conjugate liquid crystal tunable filter, a SWIR liquid crystal tunable filter, a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter, and combinations thereof.

In one embodiment, the system and method utilize ChemImage Multi-Conjugate Filter ("MCF") technology available from ChemImage Corporation, Pittsburgh, Pa. This technology is more fully described in U.S. Pat. No. 7,362, 489, entitled "Multi-Conjugate Liquid Crystal Tunable Filter" and U.S. Pat. No. 6,992,809, also entitled "Multi-Conjugate Liquid Crystal Tunable Filter." Both of these patents are hereby incorporated by reference in their entireties.

In one embodiment, the method may further comprise obtaining at least one of a mid wave infrared (MWIR) hyperspectral image, a long wave infrared (LWIR) hyperspectral image, and combinations thereof. The use of LWIR spectroscopy and imaging techniques may be used to detect human presence in a scene and human movement in a scene. This use of LWIR may be used in conjunction with motion sensing to thereby configure laser interlocking. This effectively turns off a laser when a human is present. This holds potential for increasing safety, including eye safety, of the system and method disclosed herein.

Figure 3:
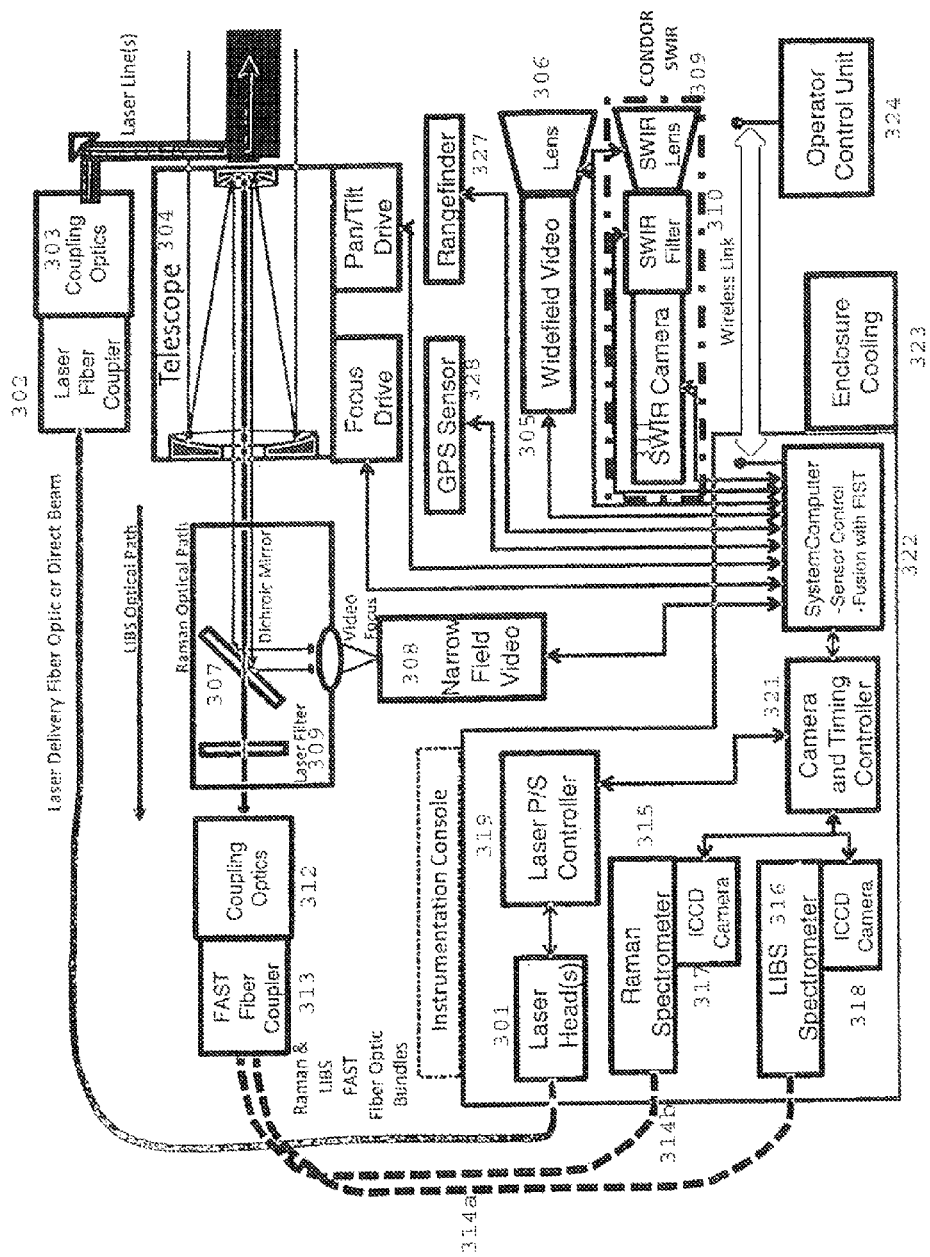
FIG. 3 is a schematic representation of a system of the present disclosure.

The present disclosure also provides for a system for the detection and identification of explosive and other materials. In one embodiment, the system of the present disclosure may incorporated CONDOR-ST technology available from ChemImage Corporation, Pittsburgh, Pa. One embodiment of a system of the present disclosure is illustrated in FIG. 3. In one embodiment, the system 300 may comprise a first optical system optically coupled to an illumination source, which is illustrated in FIG. 3 as laser head 301. In addition to laser head 301 the system may utilize at least one of: a broadband light source and an ambient light source. In one embodiment, the laser head 310 may be coupled to a laser controller 319 for configuring the laser. In some embodiments, it may not be required for the illumination source to be physically coupled to the system 300, for example when an ambient light source such as the sun is used as an illumination source. The first optical system may comprise a laser fiber coupler 302, a coupling optics 303, and a telescope 304.

In one embodiment, the components of the first optical system are matched to one or more mirrors of the telescope, and expand the laser beam to fill the mirror. The laser excitation pulse may propagate along the telescope's optical axis and present a laser spot that dills the telescope's field of view at the chosen focal point. This allows for a 180° backscattering collection geometry and enables repositioning and refocusing of the telescope 304 and laser spot simultaneously.

The system 300 may further comprise a visible imaging device, which is illustrated in FIG. 3 as a video capture device 305. The video capture device 305 may be configured to output a dynamic image of the region of interest and/or target area in real time. This video capture device 305 may be configured to operate in a targeting mode in which it surveys a region of interest/target area. Video is highly sensitive but may have a low specificity, in that it provides for a low level means of classifying objects based on morphological factors such a size, shape, and color. Such first-order discrimination may provide good guidance for higher order classification and detection such as Raman, SWIR, and/or LIBS spectroscopy and imaging. In one embodiment, the video capture device 305 may utilize a target scope to provide for a large area of view and zoom control. In one embodiment, this target scope may be incorporated into the lens 306 associated with the video capture device 305. The system 300 may further comprise a narrow field video device 320 for obtaining additional video data.

The video capture device 305 may use ambient light or light from laser light source 301 to illuminate the target area. The video capture device 305 may also collect a series of small images, that are recombined into a larger, macro-image for analysis. The video capture device 305 operates in the first order targeting mode to rapidly screen objects based on the intrinsic size, shape and color properties of the particles. Regions of interest suspected to possess explosive residues are located and identified, honing in on the target area at which to conduct further analysis using LIBS/Raman imaging spectroscopy that provide greater specificity.

The system 300 may also comprise a second optical system that collects at least one of photons reflected, scattered, and/or plasma emitted by a region of interest and/or target area. This second optical system may direct the collected reflected photons to a first two-dimensional array of detection elements for SWIR spectroscopic analysis. This second optical system may direct the collected scattered and/or plasma emitted photons to a fiber array spectral translator device. The second optical system may comprise a telescope 304, a mirror 307, a filter 309, and a coupling optics 312. In one embodiment, the system may further comprise a dichroic beam splitter. In one embodiment, this dichroic beam splitter may enable simultaneous Raman acquisition and visual targeting.

Alternatively, a lens 309 can collect reflected photons from a region of interest and/or target area and direct the reflected photons to a SWIR filter 310 which may comprise at least one of a SWIR liquid crystal tunable and SWIR multi-conjugate liquid crystal tunable filter. The SWIR filter 310 may effectively filter a plurality of reflected photons into a plurality of wavelength bands. The wavelength hands include wavelengths characteristic of the sample undergoing analysis. The wavelengths that can be passed through a tunable filter may range from 200 nm (ultraviolet) to 2000 nm (far infrared). The choice of a tunable filter depends on the desired optical region and/or the nature of the sample being analyzed. The reflected photons may then be detected at a SWIR detector, shown in FIG. 3 as a SWIR camera 311. The SWIR camera 311 may be configured to output a dynamic image of the region of interest/target area. The SWIR camera 311 may also be configured to output at least one of: a SWIR hyperspectral image, a plurality of spatially resolved SWIR spectra, and a plurality of spatially resolved SWIR images. The SWIR camera 311 may be configured to operate in real-time. The lens 309 may be configured to be operatively coupled to telescope optics to thereby increase the magnification and sensitivity of SWIR detection. Telescope optics may also be used to increase illumination NA to decrease NOHD.

The second optical system's coupling optics 312 may be operatively coupled to fiber array spectral translator device comprising a fiber array spectral translator device fiber coupler 313 and fiber array spectral translator fiber optic bundles 314a and 314b. One end of said fiber optic bundles 314a and 314b is operatively connected to at least one spectrometer. In FIG. 3, fiber optic bundles 314a and 314b are operatively connected to one of a Raman spectrometer 315 and a LIBS spectrometer 316. In another embodiment, a Raman grating array and a LIBS grating array may be incorporated into a single spectrometer.

A Raman spectrometer 315 may disperse said scattered photons output by said fiber array spectral translator device to generate a plurality of spatially resolved Raman spectra. A Raman detector 317 may detect the spatially resolved Raman spectra. A LIBS spectrometer 316 may disperse said plasma emitted photons output by said fiber array spectral translator device to generate a plurality of spatially resolved atomic spectra. A LIBS detector may detect the spatially resolved atomic spectra.

The system 300 may also comprise a pan/tilt drive unit 326 and a focus drive unit 325 to control the operation of elements of the system 300. The system 300 may further comprise a range finer 327 and a GPS sensor 328 for finding, locating, and/or targeting. The system 300 may further comprise an operator control unit 324 for interfacing with a user and allowing the user to operate the system 300.

The system 300 may also comprise a cooling enclosure 323, a camera and timing controller coupled to one or more detectors 317 and 318, and a system computer 322. The system computer 322 may be configured to perform fusion and to control the system 300.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A system comprising:
   a first illumination source configured to illuminate a target area comprising an unknown material, to thereby generate a first plurality of interacted photons wherein said first plurality of interacted photons are selected from the group consisting of; photons reflected by said material, photons scattered by said material, photons plasma emitted by said material, and combinations thereof; a first optical system coupled to said first illumination source to direct light to the target area; a video capture device that outputs a dynamic image of said target area; a first two-dimensional array of detection elements; a second optical system that collects at least one of said reflected photons, said scattered photons, and said plasma emitted photons, and directs the collected reflected photons to said first two-dimensional array of detection elements, wherein said first two-dimensional array of detection elements is coupled to said second optical system, and further directs at least one of said scattered photons and said plasma emitted photons to a fiber array spectral translator device, wherein said fiber array spectral translator device is coupled to said second optical system; wherein said first two-dimensional array detects in a spatially accurate manner said reflected photons received from said second optical system thereby generate at least one of: a plurality of spatially accurate wavelength resolved short wave infrared images and a plurality of spatially resolved short wave infrared spectra; wherein said fiber array spectral translator device outputs at least one of the following received from said second optical system: said collected scattered photons, and said collected plasma emitted photons, and includes a two-dimensional array of optical fibers drawn into a one-dimensional fiber stack so as to effectively convert a two-dimensional field of view into a curvilinear field of view; at least one spectrometer coupled to said one-dimensional fiber stack of said fiber array spectral translator device, wherein an entrance slit of said spectrometer is coupled to said one dimensional fiber stack to perform at least one of the following: disperse said scattered photons output by said fiber array spectral translator device to generate a plurality of spatially resolved Raman spectra, and disperse said plasma emitted photons output by said fiber array spectral translator device to generate a plurality of spatially resolved atomic spectra; and a second two dimensional array of detection elements, wherein said second two dimensional array of detection elements is coupled to said spectrograph and detects at least one of: said plurality of spatially resolved Raman spectra, said plurality of spatially resolved atomic spectra, and combinations thereof.

2. The system of claim 1 wherein said second two dimensional array of detection elements comprises at least one of: a Raman detector and a LIBS detector.

3. The system of claim 2 further comprising: a Raman spectrograph configured to disperse said scattered photons output by said fiber array spectral translator device to generate a plurality of spatially resolved Raman spectra; said Raman detector configured to detect said spatially resolved Raman spectra; a LIBS spectrograph configured to disperse said plasma emitted photons output by said fiber array spectral translator device to generate a plurality of spatially resolved atomic spectra; and said LIBS detector configured to detect said spatially resolved atomic spectra.

4. The system of claim 1 wherein said first illumination source comprises at least one of: a laser light source, a broadband light source, an ambient light source, and combinations thereof.

5. The system of claim 1 wherein said illumination source illuminates said target area using at least one of: continuous wave excitation, pulsed laser excitation, and combinations thereof.

6. The system of claim 1 wherein said first illumination source illuminates said target area using structured illumination.

7. The system of claim 6 wherein said structured illumination is configured so as to provide for simultaneous acquisition of short wave infrared spectral data, Raman spectral data, and LIBS spectral data.

8. The system of claim 1 wherein said illumination source illuminates a region said target area with a first wavelength to produce said scattered photons and a region of said target area with a second wavelength to produce said plasma emitted photons.

9. The system of claim 1 wherein said illumination source is configured for illumination in a plurality of modes, wherein each mode comprises illuminating using a different excitation wavelength.

10. The system of claim 1 wherein said first optical system further comprises a telescope to locate and focus on said target area, said telescope coupled to said first optical system.

11. The system of claim 10 wherein said first optical system further comprises a collection lens.

12. The system of claim 10 wherein said first optical system further comprises a plurality of collection lenses.

13. The system of claim 1 further comprising: a Raman spectrometer for receiving said dispersed Raman photons, a Raman detector for receiving at least one of said plurality of spatially resolved Raman spectra and said plurality of spatially resolved Raman images, a LIBS spectrometer for receiving said dispersed atomic emitted photons, and a LIBS detector for receiving at least one of said plurality of spatially resolved LIBS spectra and said plurality of spatially resolved LIBS images.

14. The system of claim 1 further comprising a tunable filter placed before at least one of said first two-dimensional array of detection elements and said second two-dimensional array of detection elements.

15. The system of claim 14 wherein said tunable filter is selected from the group consisting of: a liquid crystal tunable filter, a multi-conjugate liquid crystal tunable filter, a short wave infrared multi-conjugate liquid crystal tunable filter, acousto-optical tunable filter, a electro-optical tunable filter, and combinations thereof.

16. The system of claim 1 further comprising instructions executable by at least one processor that applies a fusion algorithm to two or more of the following: said plurality of spatially resolved short wave infrared spectra, said plurality of spatially resolved atomic spectra, and said spatially resolved Raman spectra, to thereby identify said unknown material.

17. The system of claim 1 further comprising at least one processor configured to generate a plurality of control signals, wherein said control signals include: first control signals that control operation of at least said first illumination source; and second control signals that control operation of said second optical system such that the second optical system directs the collected reflected photons to a tunable filter and directs the collected scattered photons and the plasma emitted photons to said fiber array spectral translator device.

18. The system of claim 1 further comprising a means for engaging illumination source interlocking in response to detecting at least one human present in at least one of a region of interest and a target area.

19. The system of claim 1 wherein said video capture device is configured to operate in a targeting mode to thereby locate said target area.

20. The system of claim 19 wherein said target area is located based on at least one of: size of said target area, shape of said target area, color of said target area, and combinations thereof.

21. The system of claim 1 further comprising a second illumination source for illuminating said target area to thereby generate a second plurality of interacted photons wherein said second plurality of interacted photons are selected from the group consisting of: photons reflected by said material, photons scattered by said material, photons plasma emitted by said material, and combinations thereof.

22. The system of claim 21 wherein said second illumination source is selected from the group consisting of: a laser light source, a broadband light source, an ambient light source, and combinations thereof.

23. The system of claim 1 further comprising a means for configuring gated detection of at least one of: said reflected photons, said scattered photons, said plasma emitted photons, and combinations thereof.

24. The system of claim 1 wherein said unknown material comprises at least one of: a chemical threat agent, a biological threat agent, an explosive threat agent, a non-threat agent, a material associated with a threat agent, and combinations thereof.

25. The system of claim 17 wherein said system further comprises a telescope to locate and focus on said target area, wherein said first control signals further control operation of said telescope.

26. The system of claim 14 further comprising third control signals that control operation of said tunable filter such that said tunable filter sequentially filters collected reflected photons in each of a plurality of predetermined wavelength bands.

* * * * *